US008747695B2

(12) United States Patent
Jasper et al.

(10) Patent No.: US 8,747,695 B2
(45) Date of Patent: Jun. 10, 2014

(54) COMPOUNDS FOR A LIQUID-CRYSTALLINE MEDIUM, AND USE FOR HIGH-FREQUENCY COMPONENTS

(75) Inventors: Christian Jasper, Darmstadt (DE); Elvira Montenegro, Weinheim (DE); Detlef Pauluth, Ober-Ramstadt (DE); Volker Reiffenrath, Rossdorf (DE); Atsutaka Manabe, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/503,761

(22) PCT Filed: Oct. 1, 2010

(86) PCT No.: PCT/EP2010/006014
§ 371 (c)(1),
(2), (4) Date: Jul. 20, 2012

(87) PCT Pub. No.: WO2011/047781
PCT Pub. Date: Apr. 28, 2011

(65) Prior Publication Data
US 2012/0273724 A1 Nov. 1, 2012

(30) Foreign Application Priority Data
Oct. 24, 2009 (DE) .......................... 10 2009 050 632

(51) Int. Cl.
*C09K 19/32* (2006.01)
*C09K 19/30* (2006.01)
*C09K 19/34* (2006.01)
*C09K 19/12* (2006.01)
*C07D 333/08* (2006.01)
*C07C 25/24* (2006.01)
*C07C 43/225* (2006.01)
*C07C 15/58* (2006.01)
*C07C 15/60* (2006.01)

(52) U.S. Cl.
USPC ............ 252/299.62; 252/299.61; 252/299.63; 252/299.66; 549/80; 558/411; 558/428; 568/634; 570/128

(58) Field of Classification Search
CPC ........ C07C 15/58; C07C 15/60; C07C 15/62; C09K 19/32; C09K 19/322; C09K 2019/322; C09K 2019/323; C09K 2019/328; C09K 2219/11
USPC ............ 252/299.62, 299.61, 299.63, 299.66; 568/634; 570/128; 549/80; 558/411, 558/428
See application file for complete search history.

(56) References Cited

U.S. PATENT DOCUMENTS

| 5,084,204 | A | * | 1/1992 | Reiffenrath et al. ..... 252/299.62 |
| 7,361,288 | B2 | | 4/2008 | Lussem et al. |
| 8,217,389 | B2 | | 7/2012 | Nakano et al. |
| 8,465,672 | B2 | | 6/2013 | Lietzau et al. |
| 2005/0067605 | A1 | | 3/2005 | Lussem et al. |
| 2010/0012929 | A1 | | 1/2010 | Nakano et al. |
| 2010/0039684 | A1 | | 2/2010 | Kolb et al. |
| 2011/0253934 | A1 | | 10/2011 | Lietzau et al. |

FOREIGN PATENT DOCUMENTS

| CN | 101506189 A | 8/2009 |
| CN | 101523631 A | 9/2009 |
| DE | 10 2004 029 429 A1 | 2/2005 |
| EP | 2 073 290 A1 | 6/2009 |
| JP | 2004-82439 A | 3/2004 |
| WO | WO 2008/021208 A2 | 2/2008 |

OTHER PUBLICATIONS

International Search Report of PCT/EP2010/006014 (Nov. 12, 2010).
A. Gaebler et al., "Liquid Crystal-Reconfigurable Antenna Concepts for Space Applications at Microwave and Millimeter Waves", International Journal of Antennas and Propagation, vol. 2009, Article ID 876989 (2008) pp. 1-7.
T. Yatabe et al., "Liquid Crystalline Conjugated Oligomers: Synthesis and Mesomorphic Properties of Laterally and Terminally Alkyl-Substituted Oligo (1,4-Phenyleneethynylene)s", Journal of Materials Chemistry, vol. 18 (Jan. 1, 2008) pp. 4468-4477.
S. Gauza et al., "Super High Birefringence Isothiocyanato Biphenyl-Bistolane Liquid Crystals", Japanese Journal of Applied Physics, vol. 43, No. 11A (2004) pp. 7634-7638.
S. T. Wu et al., "High Birefringence and Wide Nematic Range Bis-Tolane Liquid Crystals", Applied Physics Letters, vol. 74, No. 3 (Jan. 18, 1999) pp. 344-346.
Office Action for related Chinese Patent Application No. 201080047409.9 dated Nov. 20, 2013.
Lydon, D. P. et al., "A simple 'palladium-free' synthesis of phenyleneethynylene-based molecular materials revisted," New J. Chem., 2005, vol. 29, pp. 972-976.

* cited by examiner

*Primary Examiner* — Shean C Wu
(74) *Attorney, Agent, or Firm* — Millen, White, Zelano & Branigan, P.C.

(57) ABSTRACT

The present invention relates to compounds of the formula (I)

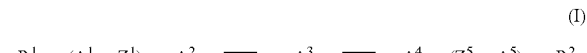

where one or more of the radicals $A^{1-5}$ denote a 1,4-naphthylene or 1,4-anthracenylene radical, and the other parameters are as defined in Claim 1. The invention additionally includes liquid-crystalline media which comprise the title compounds, components for high-frequency technology which comprise these media, in particular phase shifters and microwave array antennae.

20 Claims, No Drawings

COMPOUNDS FOR A LIQUID-CRYSTALLINE MEDIUM, AND USE FOR HIGH-FREQUENCY COMPONENTS

The present invention relates to novel chemical compounds containing two or more C—C triple bonds and at least one 1,4-naphthylene radical or 1,4-anthracenylene radical, to liquid-crystalline media composed thereof and to high-frequency components comprising these media, in particular antennae, especially for the gigahertz range. The liquid-crystalline media serve, for example, for the phase shifting of microwaves for tuneable "phased-array" antennae or for tuneable cells of microwave antennae based on "reflectarrays".

Liquid-crystalline media have been used for some time in electro-optical displays (liquid crystal displays—LCDs) in order to display information.

Recently, however, liquid-crystalline media have also been proposed for use in components for microwave technology, such as, for example, in DE 10 2004 029 429 A and in JP 2005-120208 (A).

An industrially valuable application of liquid-crystalline media in high-frequency technology is based on their property that their dielectric properties can be controlled, particularly for the gigahertz range, by a variable voltage. This enables the construction of tuneable antennae which do not contain any moving parts (A. Gaebler, A. Moessinger, F. Goelden, et al., "Liquid Crystal-Reconfigurable Antenna Concepts for Space Applications at Microwave and Millimeter Waves", International Journal of Antennas and Propagation, Vol. 2009, article ID 876989, 7 pages, 2009, doi: 10.1155/2009/876989).

A. Penirschke, S. Müller, P. Scheele, C. Weil, M. Wittek, C. Hock and R. Jakoby: "Cavity Perturbation Method for Characterization of Liquid Crystals up to 35 GHz", 34th European Microwave Conference—Amsterdam, pp. 545-548, describe, inter alia, the properties of the known single liquid-crystalline substance K15 (Merck KGaA, Germany) at a frequency of 9 GHz.

1-(Phenylethynyl)tolans, also called bistolan compounds below, are known to the person skilled in the art. For example, Wu, S.-T., Hsu, C.-S., Shyu, K.-F., Appl. Phys. Lett., 74 (3), (1999), 344-346, disclose various liquid-crystalline bistolan compounds containing a lateral methyl group, of the formula

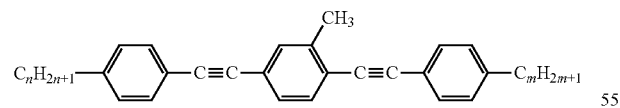

A compound of the formula

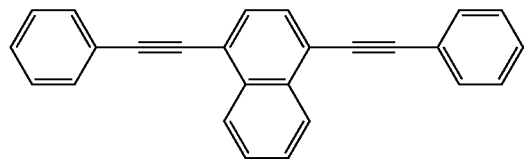 [SMILES: C(#Cc1ccc(C#Cc2ccccc2)c2ccccc12)c1ccccc1]

or derivatives thereof are described as constituents of organic thin-film transistors (EP 2 073 290 A1), as photosensitising dyes for the control of photoacid generating systems (WO 2008/021208 A2) and as constituents of data recording media (JP 2004-082439 A). Liquid-crystalline properties and the use thereof in liquid-crystalline media have not been described to date.

DE 10 2004 029 429 A describes the use of conventional liquid-crystal media in microwave technology, inter alia in phase shifters. This document has already investigated liquid-crystalline media with respect to their properties in the corresponding frequency range.

However, the compositions or individual compounds known to date are generally afflicted with disadvantages. Most of them result, besides other deficiencies, in disadvantageously high losses and/or inadequate phase shifts or inadequate material quality.

For use in high-frequency technology, liquid-crystalline media having particular, hitherto rather unusual, uncommon properties, or combinations of properties, are required.

Novel components for liquid-crystalline media having improved properties are thus necessary. In particular, the loss in the microwave range must be reduced and the material quality ($\eta$) improved.

In addition, there is a demand for an improvement in the low-temperature behaviour of the components. An improvement in both the operating properties and the shelf life is necessary here.

Thus, there is a considerable demand for liquid-crystalline media having suitable properties for corresponding practical applications.

Surprisingly, it has now been found that it is possible, using the compounds according to the invention, to achieve liquid-crystalline media having a suitable nematic phase range and high $\Delta n$ which do not have the disadvantages of the prior-art materials, or at least only do so to a considerably reduced extent.

The invention relates to compounds of the formula I

in which
$A^{1-5}$, independently of one another, denote
  a) a radical of the formulae

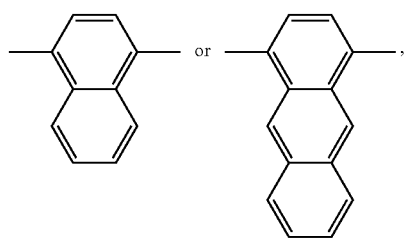

b) 1,4-phenylene, in which one or more, preferably one to two, CH groups may be replaced by N, c) trans-1,4-cyclohexylene or cyclohexenylene, in which, in addition, one or two non-adjacent CH$_2$ groups may be replaced by —O— and/or —S— and in which H may be replaced by F, or d) a radical from the group 1,4-bicyclo[2.2.2]octylene, cyclobut-1,3-diyl, spiro[3.3]heptane-2,6-diyl, thiophene-2,5-diyl, thiophene-2,4-diyl, furan-2,5-diyl, furan-2,4-diyl,

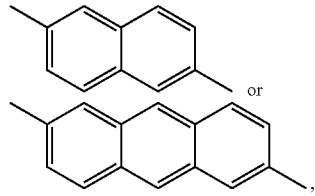

or and in which, in groups a), b), c) and d), one or more H atoms may also be replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group, and where at least one radical from A$^1$ to A$^5$, preferably from A$^2$, A$^3$ and A$^4$, represents a radical according to a), R$^1$ and R$^2$ each, independently of one another, denote a halogenated or unsubstituted alkyl radical having 1 to 15 C atoms, where, in addition, one or more CH$_2$ groups in these radicals may each be replaced, independently of one another, by —C≡C—, —CH═CH—, —CF═CF—, —CF═CH—, —CH═CF—, —(CO)O—, —O(CO)—, —(CO)—, —O— or —S— in such a way that O or S atoms are not linked directly to one another, F, Cl, Br, CN, CF$_3$, OCF$_3$, SCN, NCS or SF$_5$, Z$^1$, Z$^5$, independently of one another, denote a single bond, —C≡C—, —CH═CH—, —CH$_2$O—, —(CO)O—, —CF$_2$O—, —CF$_2$CF$_2$—, —CH$_2$CF$_2$—, —CH$_2$CH$_2$—, —(CH$_2$)$_4$—, —CH═CF— or —CF═CF—, where asymmetrical bridges may be oriented to both sides, and m, n, independently of one another, denote 0, 1 or 2, where compounds of the formula I-X-1,

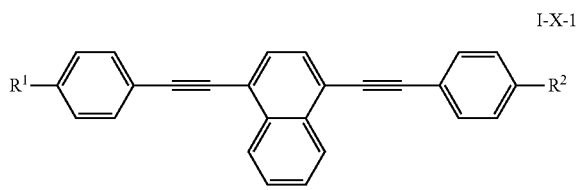

in which

R$^1$ and R$^2$ are each simultaneously CH$_3$, n-C$_6$H$_{11}$, CF$_3$, F or OCH$_3$, or R$^1$ denotes tert-butyl and R$^2$ denotes —CN, and the compound of the formula I-X-2

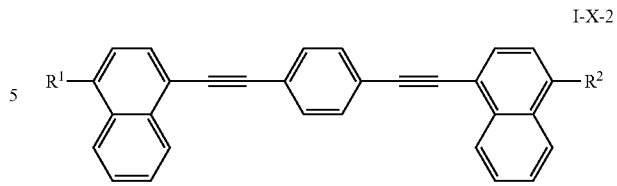

in which

R$^1$ and R$^2$ simultaneously denote n-C$_4$H$_9$, are excluded.

The compounds of the formula I-X-1 are disclosed in the document EP 2073290 A1, WO 2008/021208 or JP 2004-82439 A, those of the formula I-X-2 are disclosed in JP 2004-82439 A.

The compounds according to the invention have a high clearing point, extraordinarily high optical anisotropy (Δn) and advantageous high rotational viscosity. Alone or in a mixture with further mesogenic components, they have a nematic phase over a broad temperature range. These properties make them particularly suitable for use in components for high-frequency technology, in particular in liquid-crystalline phase shifters.

Preferably, one or two of the radical from A$^2$, A$^3$ and A$^4$ represent(s) an optionally substituted radical in accordance with definition a) of the radicals, particularly preferably one. Particularly preferably, at least the radical A$^3$ is a radical in accordance with definition a). Of the radicals from group a), the 1,4-naphthylene radical is particularly preferred.

The index m is preferably 0 or 1, particularly preferably 0. The index n is preferably 0 or 1, particularly preferably 0. The sum of m and n is preferably 0 or 1.

The ring groups A$^1$ and A$^5$ are preferably a 1,4-phenylene, in which, in addition, one or more H atoms may be replaced by Br, Cl, F, CN, alkyl (C$_1$-C$_{10}$), methoxy or a mono- or polyfluorinated methyl or methoxy group.

The bridge groups Z$^1$ and Z$^5$ are preferably a single bond, —C≡C— or —CH═CH—, particularly preferably a single bond.

One of the radicals R$^1$ or R$^2$, preferably R$^1$, preferably denotes a straight-chain alkyl radical having 1 to 15 C atoms, where, in addition, one or more CH$_2$ groups in these radicals may each be replaced, independently of one another, by —C≡C—, —CH═CH—, —(CO)O—, —O(CO)—, —(CO)— or —O— in such a way that O atoms are not linked directly to one another. R$^2$ particularly preferably denotes an alkyl radical having 2 to 5 C atoms, where, in addition, one or more CH$_2$ groups in this radical may each be replaced, independently of one another, by —C≡C—, —CH═CH—, —CF═CF—, —CF═CH—, —CH═CF—, —(CO)O—, —O(CO)— or —(CO)— in such a way that O atoms are not linked directly to one another, or F, Cl, Br, CF$_3$, OCF$_3$, SCN, NCS or SF$_5$. Preferably, none or only one of the radicals R$^{1/2}$ adopts a meaning selected from F, Cl, Br, CN, CF$_3$, OCF$_3$, SCN, NCS or SF$_5$.

Preferred embodiments of the invention are therefore selected from the following illustrative structures:
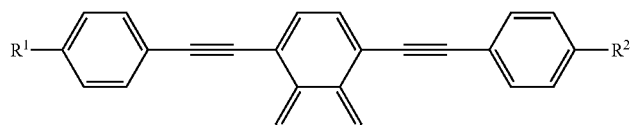
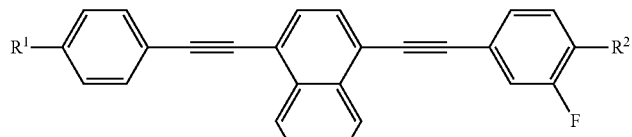
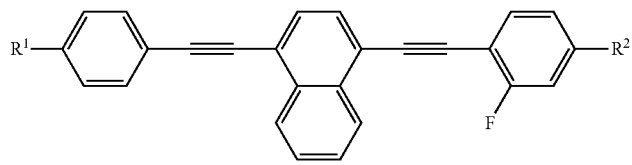
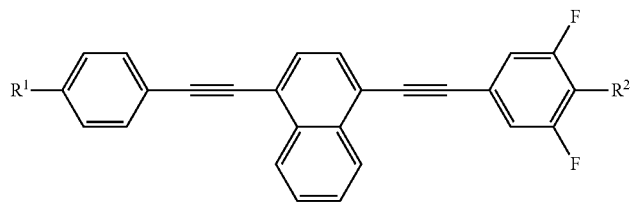
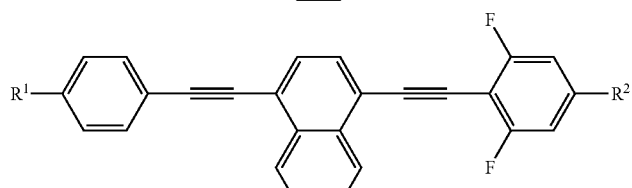
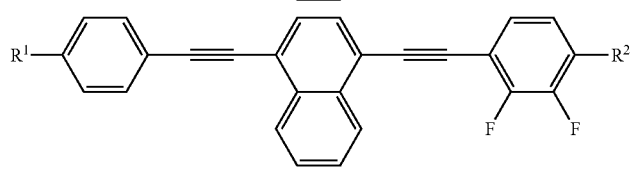
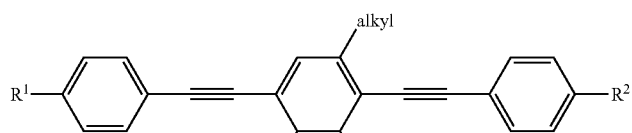
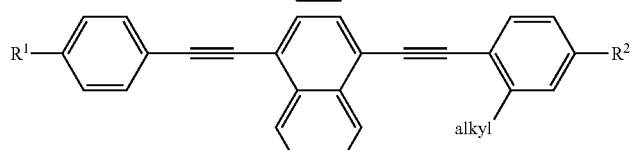
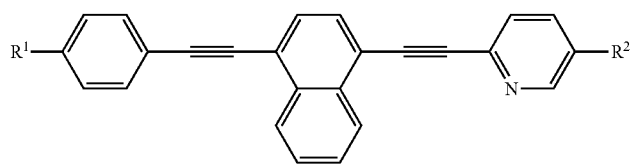

-continued
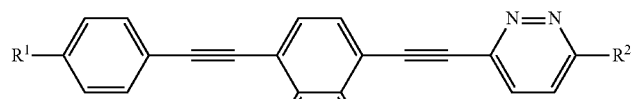
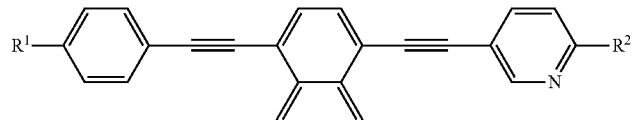
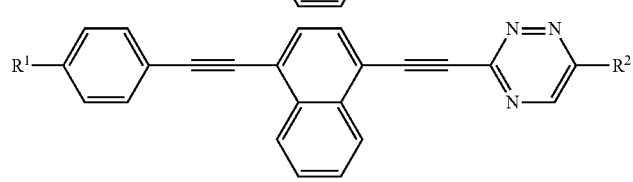
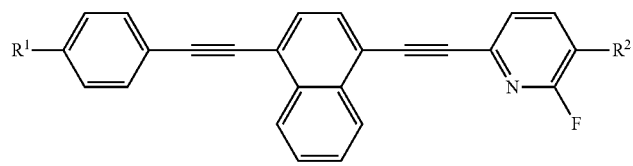
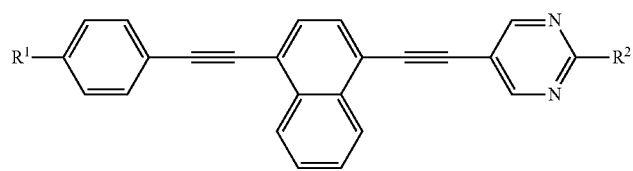
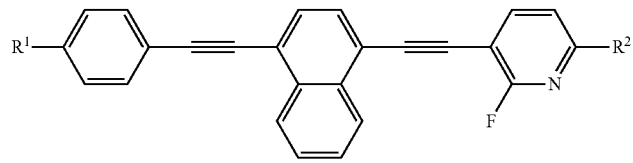
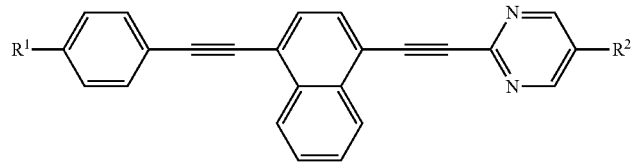
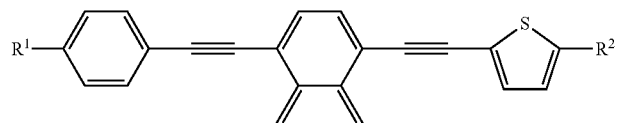
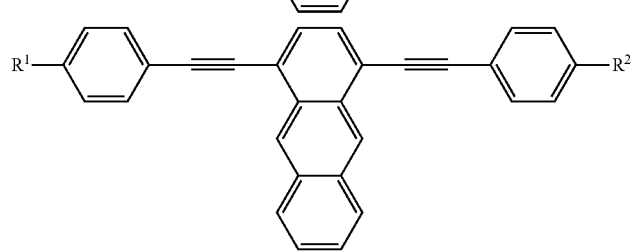

-continued
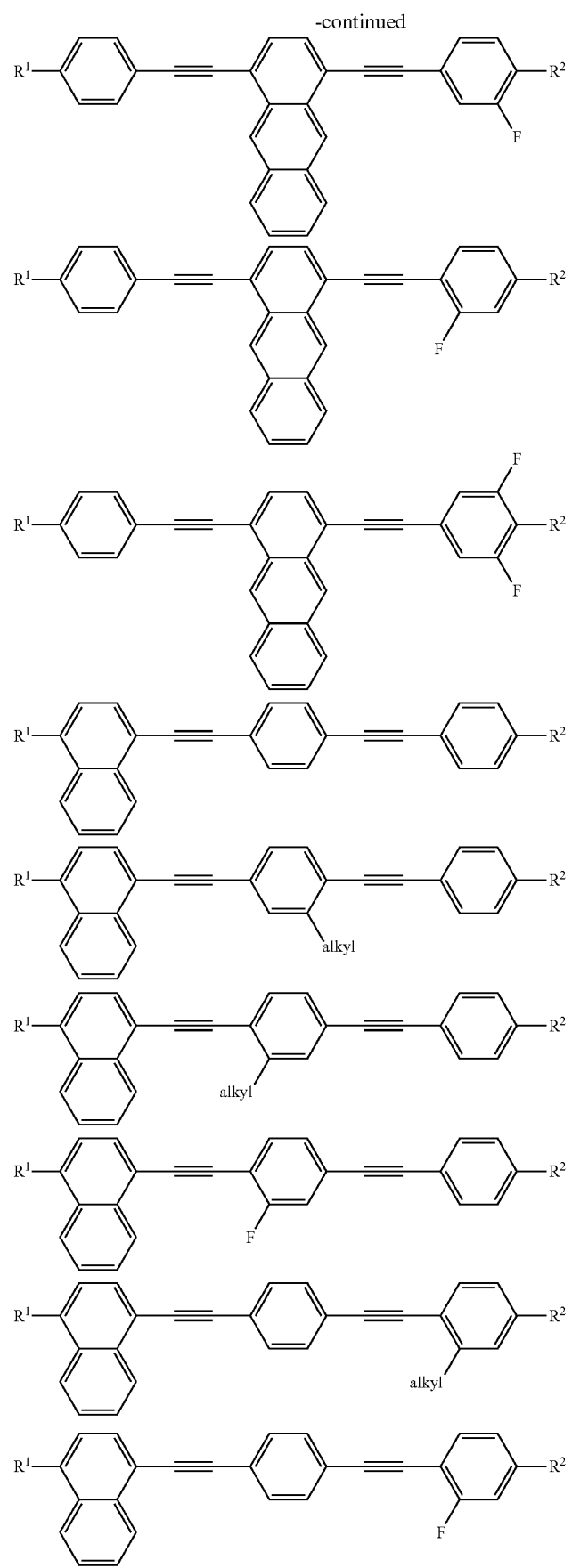

-continued
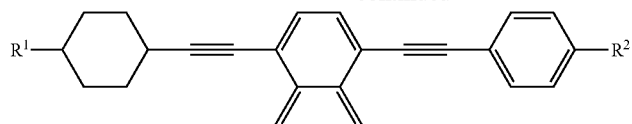
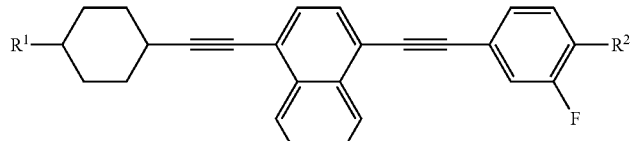
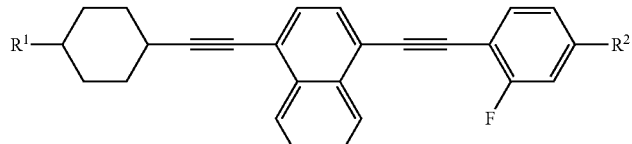
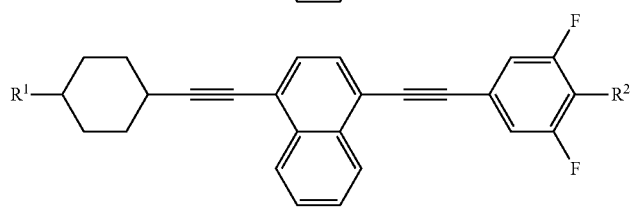
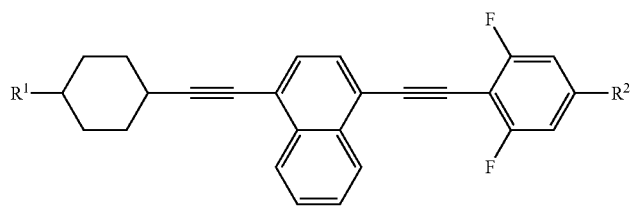
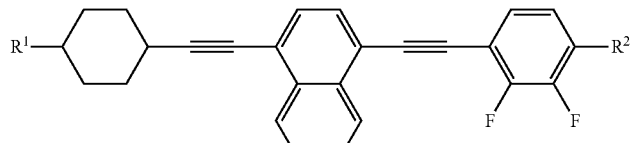
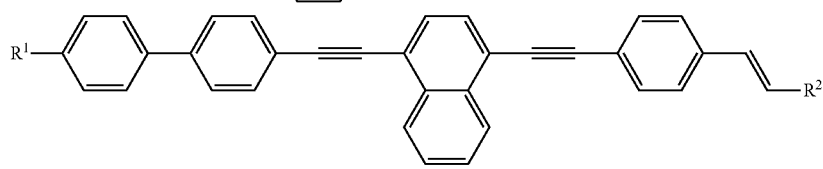
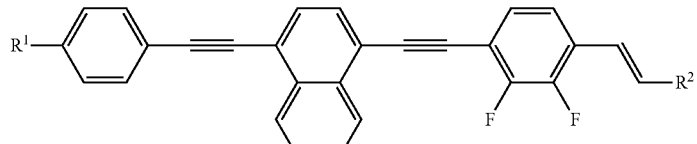
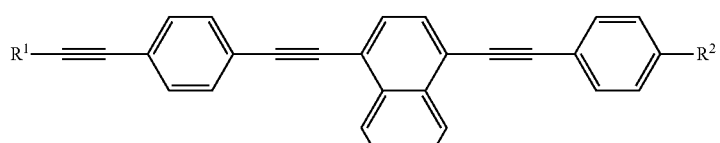
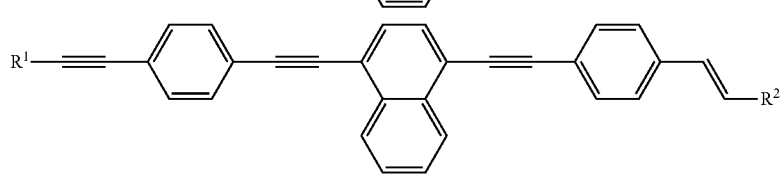

-continued
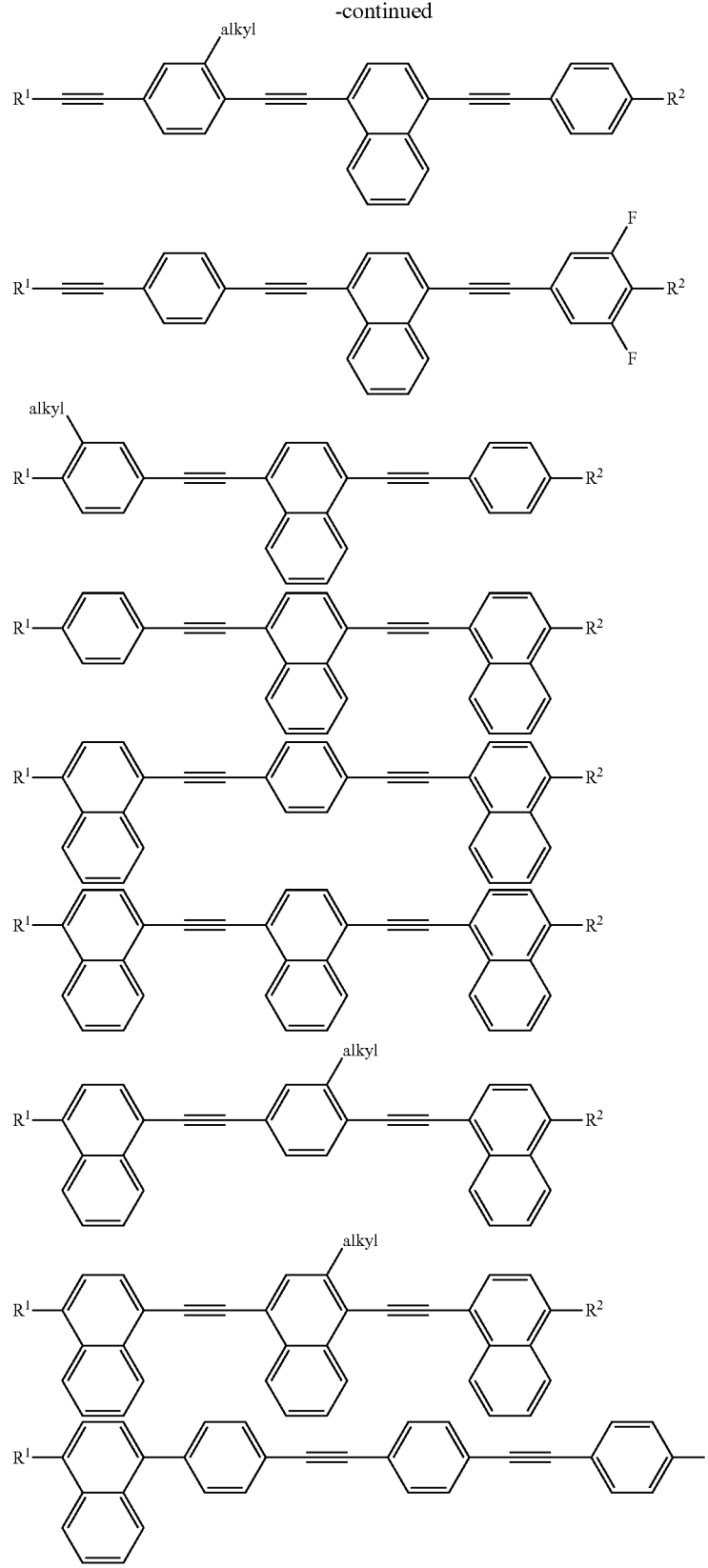
in which R¹ and R² are as defined above and "alkyl" denotes an alkyl group having 1-10 C atoms.

In a further preferred embodiment, the compounds according to the invention have clearly positive dielectric anisotropy (Δε). Corresponding compounds preferably have a structure of the formula IA or IB:

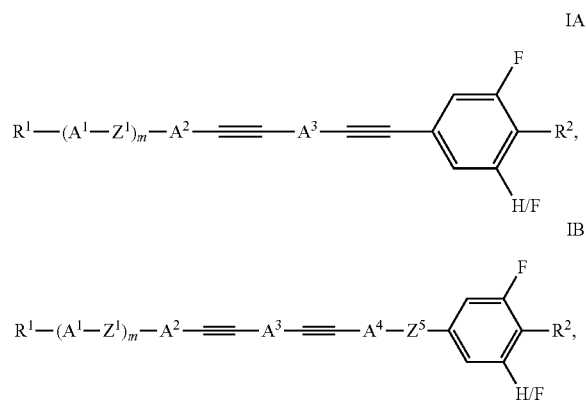

and in particular of the formula IA-1:

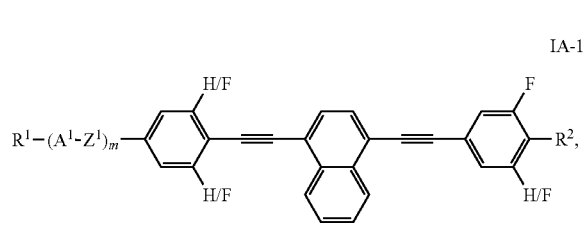

in which in each case $R^1$, $A^1$, $A^2$, $A^3$, $A^4$, $Z^1$, $Z^5$ and m are as defined above for formula I and $R^2$ denotes F, Cl, Br, CN, $CF_3$, $OCF_3$, SCN, NCS or $SF_5$.

The compounds of the formula I can advantageously be prepared as can be seen in the following illustrative synthesis (Scheme 1):

1,4-Dibromonaphthalene is subjected to a halogen-metal exchange reaction and converted into 1-iodo-4-bromonaphthalene. This is firstly converted selectively into the monofunctionalised acetylene-bridged compound in a Sonogashira coupling, followed by a second Sonogashira reaction, giving the target compounds of the formula (1) containing two acetylene bridges. If the two groups R are identical, a coupling reaction with two equivalents of the acetylene compound can be carried out directly instead of the iodination. In the case of the anthracene derivatives, corresponding halogen derivatives are used as starting material.

The liquid-crystalline media in accordance with the present invention comprise one or more compounds of the formula I and optionally at least one further, preferably mesogenic compound. The liquid-crystal medium therefore preferably comprises two or more compounds, which are preferably liquid-crystalline. The compounds of the formula I-X-1 and I-X-2 are included in the liquid-crystalline media. Preferred media comprise the preferred compounds of the formula I.

Further components of the liquid-crystalline media are preferably selected from the compounds of the formula II:

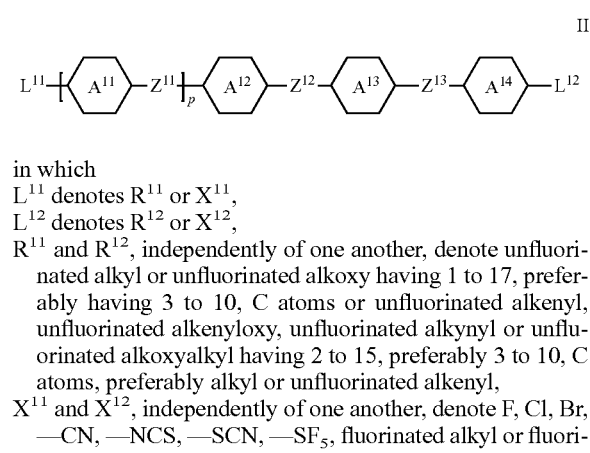

in which
$L^{11}$ denotes $R^{11}$ or $X^{11}$,
$L^{12}$ denotes $R^{12}$ or $X^{12}$,
$R^{11}$ and $R^{12}$, independently of one another, denote unfluorinated alkyl or unfluorinated alkoxy having 1 to 17, preferably having 3 to 10, C atoms or unfluorinated alkenyl, unfluorinated alkenyloxy, unfluorinated alkynyl or unfluorinated alkoxyalkyl having 2 to 15, preferably 3 to 10, C atoms, preferably alkyl or unfluorinated alkenyl,
$X^{11}$ and $X^{12}$, independently of one another, denote F, Cl, Br, —CN, —NCS, —SCN, —$SF_5$, fluorinated alkyl or fluori- Scheme 1. Illustrative synthesis of the compounds of the formula I (asymmetrical); R defined in accordance with $R^{1/2}$.

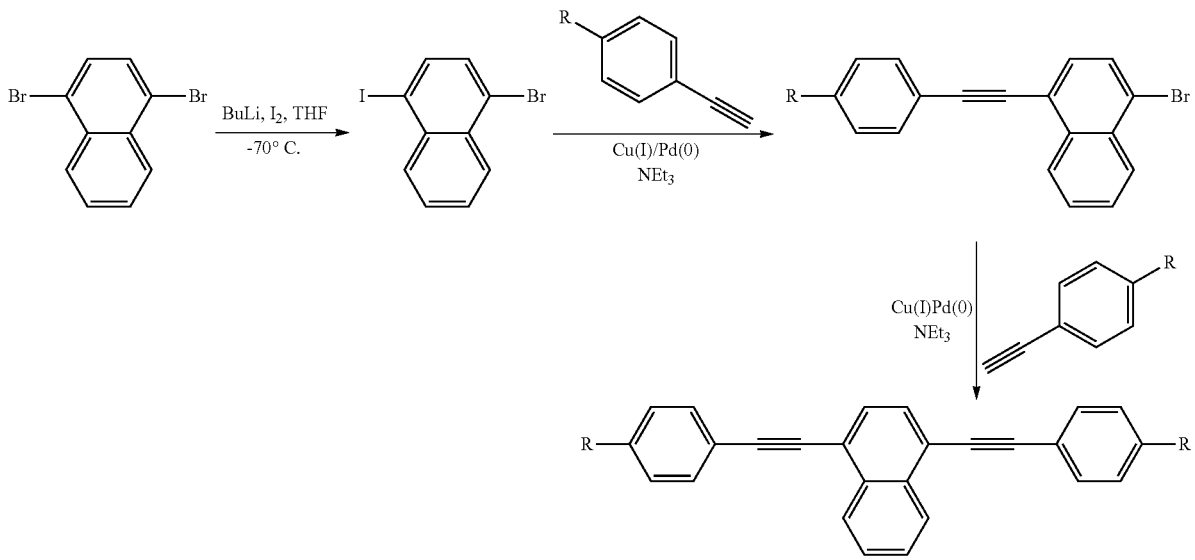

nated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F or Cl, and p denotes 0 or 1, $Z^{11}$ to $Z^{13}$, independently of one another, denote trans-CH=CH—, trans-CF=CF—, —C≡C— or a single bond, and

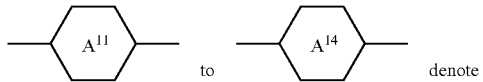

to denote a) 1,4-phenylene, in which one or more, preferably one to two, CH groups may be replaced by N, b) trans-1,4-cyclohexylene or cyclohexenylene, in which, in addition, one or two non-adjacent $CH_2$ groups may be replaced by —O— and/or —S— and in which H may be replaced by F, and in which, in groups a) and b), one or more H atoms may also be replaced by Br, Cl, F, CN, —NCS, —SCN, $SF_5$, $C_1$-$C_{10}$ alkyl, $C_1$-$C_{10}$ alkoxy, a mono- or polyfluorinated $C_1$-$C_{10}$ alkyl or alkoxy group or a $C_{3-6}$ cycloalkyl group, preferably, independently of one another, denote

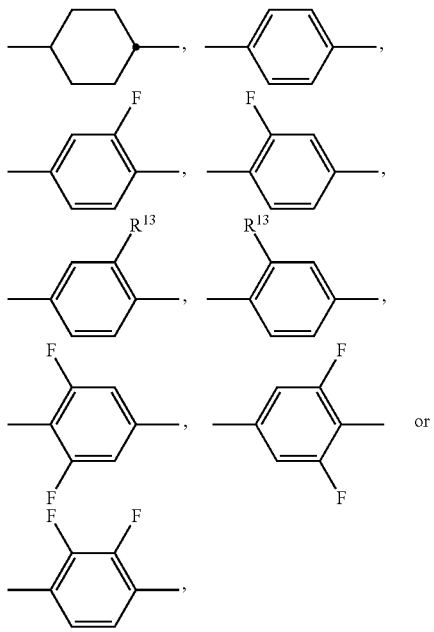

where $R^{13}$ denotes Cl, $C_{1-7}$-alkyl or $C_{3-6}$ cycloalkyl.

In a preferred embodiment of the present invention, the liquid-crystalline media comprise one or more compounds of the formula I and one or more compounds of the formula II.

The liquid-crystalline media in accordance with the present application preferably comprise in total 5 to 95%, preferably 10 to 90% and particularly preferably 15 to 80%, of compounds of the formula I.

The liquid-crystalline media in accordance with the present invention preferably comprise 10% or less, preferably 5% or less, particularly preferably 2% or less, very particularly preferably 1% or less, and in particular absolutely no compound having only two or fewer five- and/or six-membered rings.

The liquid-crystalline media in accordance with the present invention preferably comprise, more preferably predominantly consist of, even more preferably essentially consist of and very preferably completely consist of compounds selected from the group of the compounds of the formulae I and II.

In this application, "comprise" in connection with compositions means that the entity in question, i.e. the medium or the component, comprises the component or components or compound or compounds indicated, preferably in a total concentration of 10% or more and very preferably 20% or more.

In this connection, "predominantly consist of" means that the entity in question comprises 55% or more, preferably 60% or more and very preferably 70% or more, of the component or components or compound or compounds indicated.

In this connection, essentially consist of means that the entity in question comprises 80% or more, preferably 90% or more and very preferably 95% or more, of the component or components or compound or compounds indicated.

In this connection, completely consist of means that the entity in question comprises 98% or more, preferably 99% or more and very preferably 100.0%, of the component or components or compound or compounds indicated.

The liquid-crystalline media in accordance with the present application preferably comprise in total 10 to 100%, preferably 20 to 95% and particularly preferably 25 to 90%, of compounds of the formulae I and II.

In accordance with the present invention, the compounds of the formula II are preferably used in a total concentration of 10% to 90%, more preferably 15% to 85%, even more preferably 25% to 80% and very preferably 30% to 75%, of the mixture as a whole.

In addition, the liquid-crystalline media may comprise further additives, such as stabilisers, chiral dopants and nanoparticles. The individual, added compounds are employed in concentrations of 0.01 to 6%, preferably 0.1 to 3%. However, the concentration data for the remaining constituents of the liquid-crystal mixtures, i.e. the liquid-crystalline or mesogenic compounds, are indicated without taking into account the concentration of these additives.

The liquid-crystalline media preferably comprise 0 to 10% by weight, in particular 0.01 to 5% by weight and particularly preferably 0.1 to 3% by weight, of stabilisers. The media preferably comprise one or more stabilisers selected from 2,6-di-tert-butylphenols, 2,2,6,6-tetramethylpiperidines or 2-benzotriazol-2-ylphenols. These assistants are known to the person skilled in the art and are commercially available, for example as light stabilisers.

An embodiment of the invention is therefore also a process for the preparation of a liquid-crystal medium which is characterised in that one or more compounds of the formula I, as indicated in Claim 5, are mixed with one or more compounds selected from the compounds of the formula II, as indicated above, and optionally with one or more further compounds and optionally with one or more additives.

In the present application, the expression dielectrically positive describes compounds or components where $\Delta\epsilon > 3.0$, dielectrically neutral describes those where $-1.5 \leq \Delta\epsilon \leq 3.0$ and dielectrically negative describes those where $\Delta\epsilon < -1.5$. $\Delta\epsilon$ is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

$\Delta\epsilon$ is defined as $(\epsilon_\|-\epsilon_\perp)$, while $\epsilon_{average}$ is $(\epsilon_\|+2\epsilon_\perp)/3$.

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties that are typical for liquid crystals are determined in accordance with "Merck Liquid Crystals, Physical Properties of Liquid Crystals", Status November 1997, Merck KGaA, Germany, and are quoted for a temperature of 20° C., unless expressly stated otherwise. The optical anisotropy ($\Delta n$) is determined at a wave-length of 589.3 nm. The dielectric anisotropy ($\Delta\epsilon$) is determined at a frequency of 1 kHz. The threshold voltages, as well as all other electro-optical properties, are determined using test cells produced at Merck KGaA, Germany. The test cells for the determination of $\Delta\epsilon$ have a cell thickness of approximately 20 μm. The electrode is a circular ITO electrode having an area of 1.13 cm$^2$ and a guard ring. The orientation layers are SE-1211 from Nissan Chemicals, Japan, for homeotropic orientation ($\epsilon_\|$) and polyimide AL-1054 from Japan Synthetic Rubber, Japan, for homogeneous orientation ($\epsilon_\perp$). The capacitances are determined using a Solatron 1260 frequency response analyser using a sine wave with a voltage of 0.3 $V_{rms}$. The light used in the electro-optical measurements is white light. A set-up using a commercially available DMS instrument from Autronic-Melchers, Germany, is used here. The characteristic voltages are determined under perpendicular observation. The threshold ($V_{10}$), mid-grey ($V_{50}$) and saturation ($V_{90}$) voltages are determined for 10%, 50% and 90% relative contrast, respectively.

The liquid-crystalline media are investigated with respect to their properties in the microwave frequency range as described in A. Penirschke, S. Müller, P. Scheele, C. Weil, M. Wittek, C. Hock and R. Jakoby: "Cavity Perturbation Method for Characterization of Liquid Crystals up to 35 GHz", 34$^{th}$ European Microwave Conference—Amsterdam, pp. 545-548.

Compare in this respect also A. Gaebler, F. Gölden, S. Müller, A. Penirschke and R. Jakoby "Direct Simulation of Material Permittivities . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced, for example, into a polytetrafluoroethylene (PTFE) or quartz capillary. The capillary has an internal radius of 180 μm and an external radius of 350 μm. The effective length is 2.0 cm. The filled capillary is introduced into the centre of the cavity with a resonance frequency of 30 GHz. This cavity has a length of 6.6 mm, a width of 7.1 mm and a height of 3.6 mm. The input signal (source) is then applied, and the result of the output signal is recorded using a commercial vector network analyser. For other frequencies (for example 19 GHz), the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in A. Penirschke, S. Müller, P. Scheele, C. Weil, M. Wittek, C. Hock and R. Jakoby: "Cavity Perturbation Method for Characterization of Liquid Crystals up to 35 GHz", 34$^{th}$ European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnet is set correspondingly and then rotated correspondingly through 90°.

The dielectric anisotropy in the microwave range is defined as $$\Delta\epsilon_r = (\epsilon_{r,\|} - \epsilon_{r,\perp}).$$

The modulatability or tuneability ($\tau$) is defined as $$\tau = (\Delta\epsilon_r / \epsilon_{r,\|}).$$

The material quality ($\eta$) is defined as $$\eta = (\tau / \tan\delta_{\epsilon_r, max}),$$

with the maximum dielectric loss factor $\tan\delta_{\epsilon_r, max}$:

$$\tan\delta_{\epsilon_r, max} \equiv \max.\{\tan\delta_{\epsilon_r,\perp}; \tan\delta_{\epsilon_r,\|}\}$$

which arises from the maximum value of the measured values for $\tan\delta_{\epsilon_r}$.

The material quality ($\eta$) of the preferred liquid-crystal materials is 5 or more, preferably 6 or more, preferably 8 or more, preferably 10 or more, preferably 15 or more, preferably 17 or more, particularly preferably 20 or more and very particularly preferably 25 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

In the present application, the term compounds means both one compound and a plurality of compounds, unless expressly stated otherwise.

The liquid-crystal media according to the invention preferably have nematic phases of in each case at least from −20° C. to 80° C., preferably from −30° C. to 85° C. and very particularly preferably from −40° C. to 100° C. The phase particularly preferably extends to 120° C. or more, preferably to 140° C. or more and very particularly preferably to 180° C. or more. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a cell thickness of 5 µm for at least 100 hours. At high temperatures, the clearing point is measured in capillaries by conventional methods.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The Δ∈ of the liquid-crystal medium in accordance with the invention, at 1 kHz and 20° C., is preferably 1 or more, more preferably 2 or more and very preferably 3 or more.

The Δn of the liquid-crystal media in accordance with the present invention, at 589 nm (Na$^D$) and 20° C., is preferably in the range from 0.20 or more to 0.90 or less, more preferably in the range from 0.25 or more to 0.90 or less, even more preferably in the range from 0.30 or more to 0.85 or less and very particularly preferably in the range from 0.35 or more to 0.80 or less.

In a preferred embodiment of the present application, the Δn of the liquid-crystal media in accordance with the present invention is preferably 0.50 or more, more preferably 0.55 or more.

Furthermore, the liquid-crystal media according to the invention are characterised by high anisotropies in the microwave range. The birefringence is, for example, preferably 0.14 or more, particularly preferably 0.15 or more, particularly preferably 0.20 or more, particularly preferably 0.25 or more and very particularly preferably 0.30 or more, at about 8.3 GHz. In addition, the birefringence is preferably 0.80 or less.

In some embodiments, however, liquid crystals having a negative value of the dielectric anisotropy can also advantageously be used.

The liquid crystals employed are either individual substances or mixtures. They preferably have a nematic phase.

Preferred components which comprise a liquid-crystal medium or at least one compound in accordance with the invention are phase shifters, varactors, antenna arrays (for example for radio, mobile communications, microwave/radar and other data transmission), 'matching circuit adaptive filters' and others. Preference is given to components for high-frequency technology, as defined above. Preference is also given to components which can be modulated by different applied electrical voltages. Very particularly preferred components are phase shifters. In preferred embodiments, a plurality of phase shifters are functionally connected, giving, for example, a phase-controlled group antenna. A group antenna uses the phase shift of the transmitting or receiving elements arranged in a matrix in order to achieve bundling through interference. A parallel arrangement of phase shifters in row or grid form enables the construction of a so-called 'phased array', which can serve as tuneable transmitting or receiving antenna for high frequencies (for example gigahertz range). Phased array antennae according to the invention have a very broad usable reception cone.

Preferred applications are radar installations and data transmission equipment on manned or unmanned vehicles from the automobile, shipping, air-craft, space travel and satellite technology areas.

For the production of suitable components, in particular phase shifters, a liquid-crystalline medium according to the invention is typically introduced into rectangular cavities having a cross section of less than 1 mm and a length of several centimeters. The cavities have opposing electrodes mounted along two long sides. Such arrangements are familiar to the person skilled in the art. Through application of a variable voltage, the dielectric properties of the liquid-crystalline medium can be tuned in later operation in order to set different frequencies or directions of an antenna.

The term "alkyl" preferably encompasses straight-chain and branched alkyl groups having 1 to 15 carbon atoms, in particular the straight-chain groups methyl, ethyl, propyl, butyl, pentyl, hexyl and heptyl. Groups having 2 to 10 carbon atoms are generally preferred.

The term "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "alkoxy" preferably encompasses straight-chain radicals of the formula $C_nH_{2n+1}$—O—, in which n denotes 1 to 10. n is preferably 1 to 6. Preferred alkoxy groups are, for example, methoxy, ethoxy, n-propoxy, n-butoxy, n-pentoxy, n-hexoxy, n-heptoxy, n-octoxy, n-nonoxy, n-decoxy.

The term "oxaalkyl" or "alkoxyalkyl" preferably encompasses straight-chain radicals of the formula $C_nH_{2n+1}$—O—$(CH_2)_m$, in which n and m each, independently of one another, denote 1 to 10. Preferably, n is 1 and m is 1 to 6.

The term "fluorinated alkyl radical" preferably encompasses mono- or polyfluorinated radicals. Perfluorinated radicals are included. Particular preference is given to $CF_3$, $CH_2CF_3$, $CH_2CHF_2$, $CHF_2$, $CH_2F$, $CHFCF_3$ and $CF_2CHFCF_3$.

In the present application, high-frequency technology means applications having frequencies in the range from 1 MHz to 1 THz, preferably from 1 GHz to 500 GHz, more preferably 2 GHz to 300 GHz, particularly preferably from 5 to 150 GHz.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal components and liquid-crystal compounds of the liquid-crystal media in this application.

The liquid-crystal media according to the invention consist of a plurality of compounds, preferably 3 to 30, more preferably 4 to 20 and very preferably 4 to 16, compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called pre-mixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present application, high-frequency technology means applications having frequencies in the range from 1 MHz to 1 THz, preferably from 1 GHz to 500 GHz, preferably 2 GHz to 300 GHz, particularly preferably from about 5 to 150 GHz. The application is preferably in the microwave spectrum or adjacent regions suitable for communications transfer in which 'phased array' modules can be used in transmitting and receiving antennae.

In the present application and in the following examples, the structures of the liquid-crystal compounds are indicated by means of acronyms, where the transformation into chemical formulae is carried out in accordance with Tables A and B below. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}, R^{2*}, L^{1*}, L^{2*}, L^{3*}$ | $R^{1*}$ | $R^{2*}$ | $L^{1*}$ | $L^{2*}$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nN.F.F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF.F | $C_nH_{2n+1}$ | F | F | H |
| nF.F.F | $C_nH_{2n+1}$ | F | F | F |
| $nOCF_3$ | $C_nH_{2n+1}$ | $OCF_3$ | H | H |
| $nOCF_3.F$ | $C_nH_{2n+1}$ | $OCF_3$ | F | H |
| n-Vm | $C_nH_{2n+1}$ | —CH=CH—$C_mH_{2m+1}$ | H | H |
| nV-Vm | $C_nH_{2n+1}$—CH=CH— | —CH=CH—$C_mH_{2m+1}$ | H | H |

Suitable mixture components are given in Tables A and B.

TABLE A

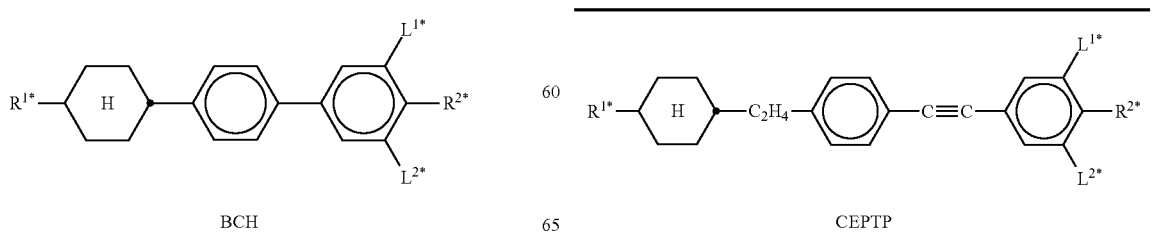

BCH

TABLE A-continued

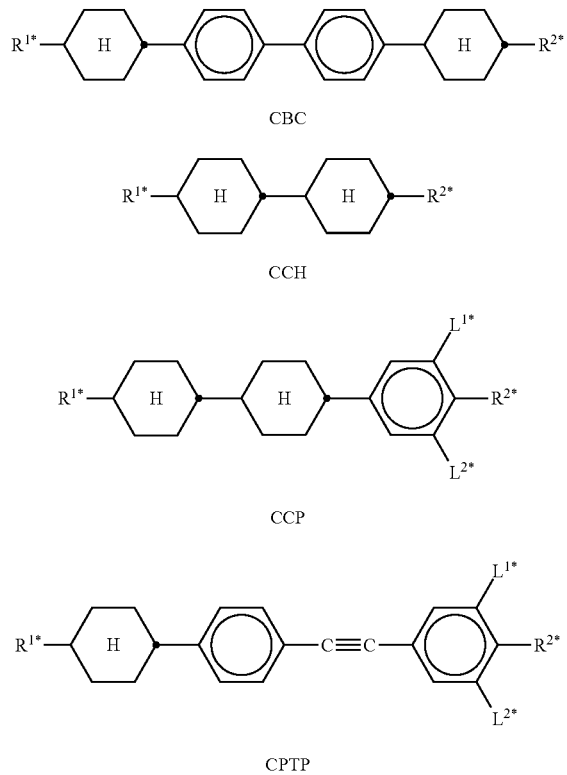

CBC

CCH

CCP

CPTP

TABLE A-continued

CEPTP

TABLE A-continued
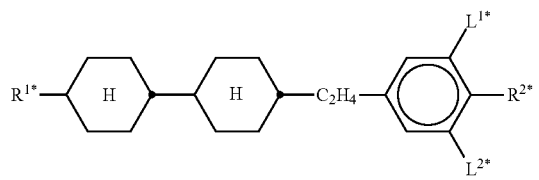
ECCP
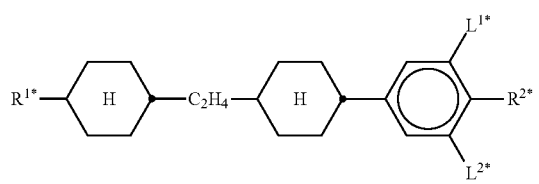
CECP
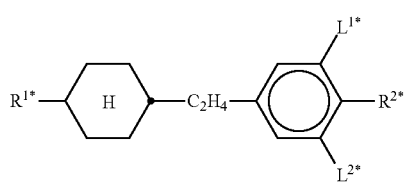
EPCH
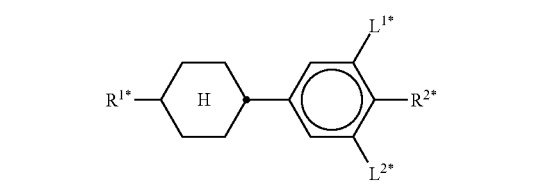
PCH
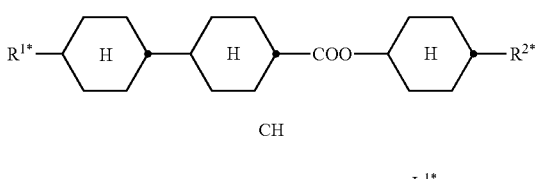
CH
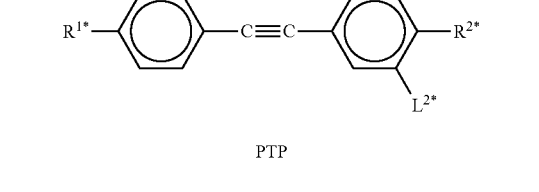
PTP
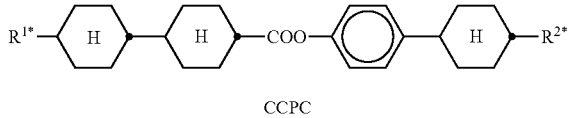
CCPC
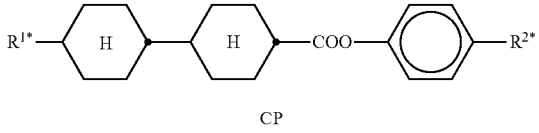
CP
TABLE A-continued
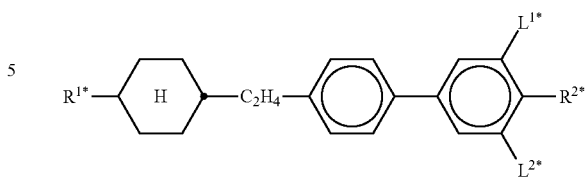
BECH
TABLE B
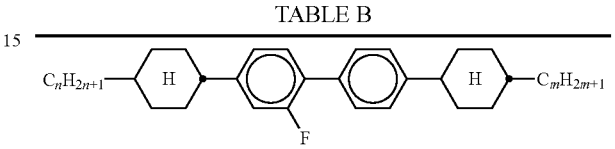
CBC-nmF
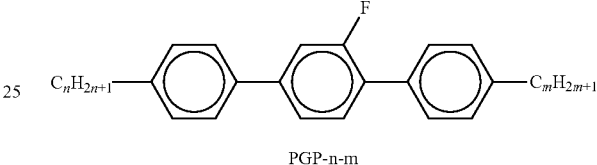
PGP-n-m
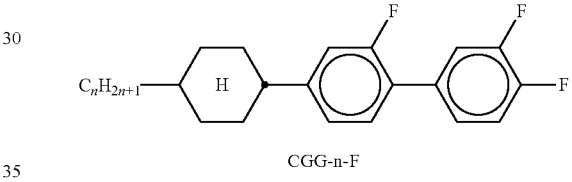
CGG-n-F
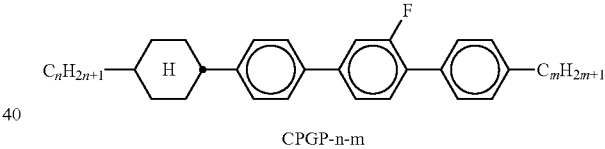
CPGP-n-m
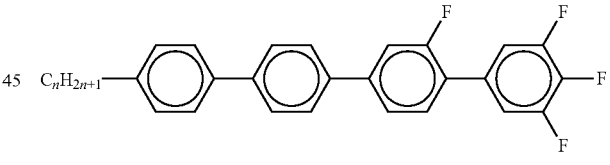
PPGU-n-F
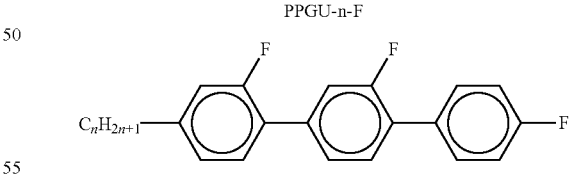
GGP-n-F
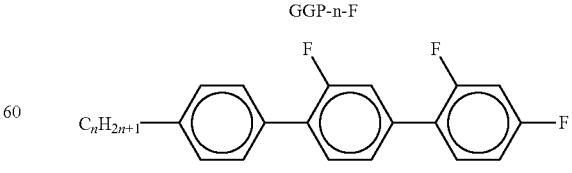
PGIGI-n-F
The following examples illustrate the present invention without limiting it in any way.

However, it becomes clear to the person skilled in the art from the physical properties what properties can be achieved and in what ranges they can be modified. In particular, the combination of the various properties which can preferably be achieved is thus well defined for the person skilled in the art.

EXAMPLES

The acetylenes employed, if not commercially available, are synthesised by standard laboratory procedures.

Synthesis Examples

1) Synthesis of 1-iodo-4-bromonaphthalene

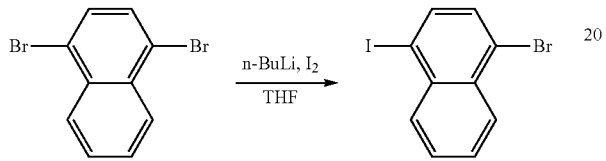

100 g (350 mmol) of 1,4-dibromonaphthalene are initially introduced in 1 l of THF, cooled to −70° C., and 235 ml of n-BuLi (1.6 M in hexane, 370 mmol) are added dropwise. After 1 h, 103 g of $I_2$ (406 mmol) in 250 ml of THF are added dropwise, the mixture is stirred at −70° C. for a further 2 h, warmed to 0° C. and quenched by the addition of 50 ml (644 mmol) of aqueous $NaHSO_3$ solution (w=39%). The phases are separated, and the aqueous phase is extracted once with MTB. The combined organic phases are washed with saturated sodium chloride solution, dried over sodium sulfate, filtered and evaporated in a rotary evaporator. The residue is purified by column chromatography ($SiO_2$, heptane), and the further purification is carried out by recrystallisation from isopropanol, giving 1-iodo-4-bromonaphthalene as a yellow solid.

2) Synthesis of 1-bromo-4-(4-n-propylphenylethynyl)naphthalene

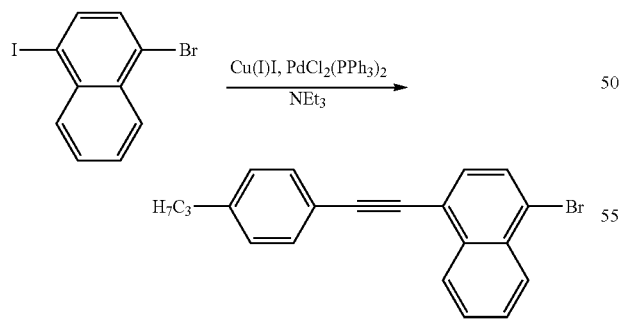

15.3 g (43.6 mmol) of 1-iodo-4-bromonaphthalene and 7.25 g (5.3 mmol) of 4-n-propylphenylacetylene are initially introduced in 200 ml of $NEt_3$, 170 mg (0.9 mmol) of copper(I) iodide and 600 mg (0.9 mmol) of bis-(triphenylphosphine) palladium(II) chloride are added, and the mixture is refluxed for 30 minutes. The batch is cooled, water and heptane are added, and the phases are separated. The organic phase is washed with saturated sodium chloride solution, dried over sodium sulfate, filtered and evaporated in a rotary evaporator. The residue is purified by column chromatography ($SiO_2$, heptane), and the further purification is carried out by recrystallisation from isopropanol.

3) Synthesis of 1-(4-n-butylphenylethynyl)-4-(4-n-propylphenylethynyl)naphthalene

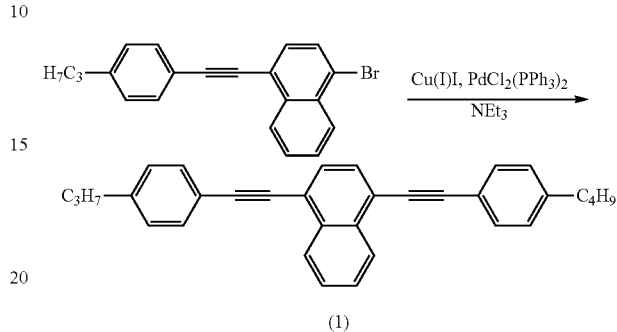

2.35 g (6.3 mmol) of 1-bromo-4-(4-n-propylphenylethynyl)naphthalene and 1.33 g (8.4 mmol) of 4-n-butylphenylacetylene are initially introduced in 40 ml of $NEt_3$, 60 mg (0.3 mmol) of copper(I) iodide and 200 mg (0.3 mmol) of bis(triphenylphosphine)palladium(II) chloride are added, and the mixture is refluxed for 18 h. The batch is cooled, water and heptane are added, and the phases are separated. The organic phase is washed with saturated ammonium chloride solution and subsequently with saturated sodium chloride solution, dried over sodium sulfate, filtered and evaporated in a rotary evaporator. The residue of compound (1) is purified by column chromatography ($SiO_2$, heptane), and the further purification is carried out by recrystallisation from isopropanol.

MS (EI): m/e (%)=426 (100, $M^+$), 397 (11, $[M-ethyl]^+$), 383 (16, $[M-propyl]^+$), 354 (18, $[M-ethyl-propyl]^+$), 177 (14, $[M-ethyl-propyl]^{2+}$).

Δ∈=+1.7
Δn=0.42
$γ_1$=1283 mPa·s
C 78 N 191 I

The following are synthesised analogously:

4) 1,4-Bis(4-n-butylphenylethynyl)naphthalene (1)

The title compound is prepared analogously to Example 3 from 1,4-dibromonaphthalene and two equivalents of 4-n-butylphenylacetylene.

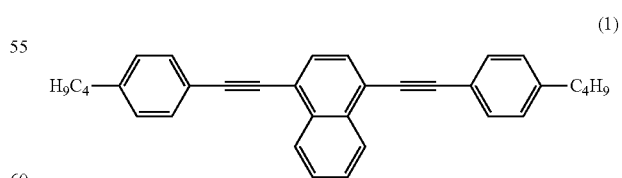

MS (EI): m/e (%)=440 (100, $M^+$), 397 (31, $[M-propyl]^+$), 354 (21, $[M-propyl-propyl]^+$), 177 (9, $[M-propyl-propyl]^{2+}$).

Δ∈=+1.2
Δn=0.41
$γ_1$=1433 mPa·s
C 75 N 176 I 5) 1-(4-n-Hexylphenylethynyl)-4-(4-n-propylphenyl-ethynyl)naphthalene

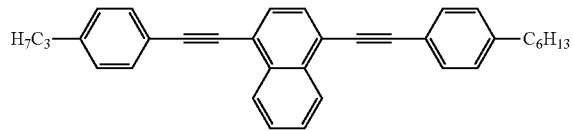

MS (EI): m/e (%)=454 (100, M$^+$), 425 (8, [M-ethyl]$^+$), 383 (22, [M-pentyl]$^+$), 354 (20, [M-pentyl-ethyl]$^+$), 177 (7, [M-pentyl-ethyl]$^{2+}$).
Δ∈=+1.2
Δn=0.41
$\gamma_1$=2067 mPa·s
C 63 N 172 I 6) 1-(4-Fluorophenylethynyl)-4-(4-n-propylphenyl-ethynyl)naphthalene

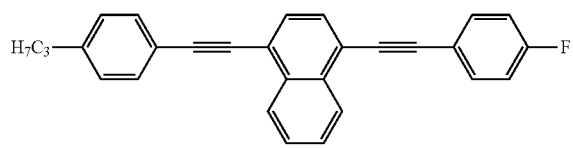

MS (EI): m/e (%)=388 (100, M$^+$), 359 (55, [M-ethyl]$^+$), 179.5 (14, [M-ethyl]$^{2+}$).
Δ∈=+5.2
Δn=0.43
$\gamma_1$=1782 mPa·s
C 103 N 188 I 7) 1-(5-Butylthiophen-2-ethynyl)-4-(4-n-propylphenylethynyl)naphthalene

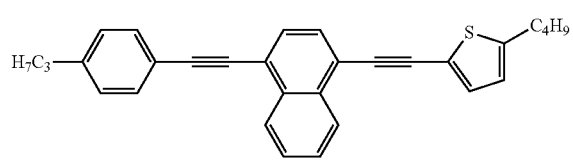

MS (EI): m/e (%)=432 (100, M$^+$), 389 (44, [M-propyl]$^+$), 360 (14, [M-propyl-ethyl]$^+$), 180 (14, [M-propyl-ethyl]$^{2+}$).
Δ∈=+2.2
Δn=0.44
$\gamma_1$=1353 mPa·s
C 67 N 107 I 8) 1,4-Bis(4-n-butylphenylethynyl)-2-methylnaphthalene

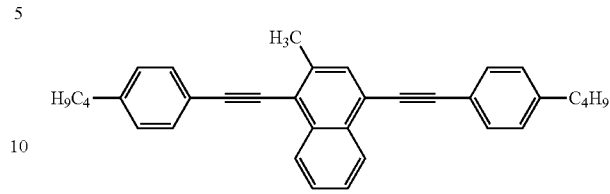

MS (EI): m/e (%)=454 (100, M$^+$), 411 (21, [M-propyl]$^+$), 368 (8 [M-propyl-propyl]$^+$), 184 [M-propyl-propyl]$^{2+}$).
Δ∈=+1.2
Δn=0.40
$\gamma_1$=3157 mPa·s
C 95 N 138 I 9) 1-(2,3-Difluoro-4-ethoxyphenylethynyl)-4-(4-n-butylphenylethynyl)naphthalene

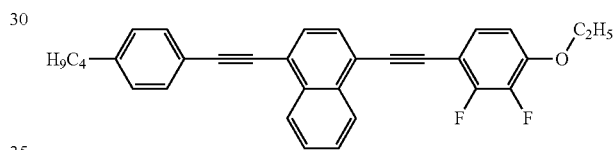

MS (EI): m/e (%)=464 (100, M$^+$), 435 (12, [M-ethyl]$^+$), 421 (10, [M-propyl]$^+$), 392 (13, [M-propyl-ethyl]$^+$), 196.5 (6, [M-propyl-ethyl]$^{2+}$).
Δ∈=−3.3
Δn=0.42
$\gamma_1$=2035 mPa·s
C 126 N 221 I 10) 1-(2,3-Difluoro-4-ethoxyphenylethynyl)-4-(trans-4-n-propylcyclohexylethynyl)naphthalene

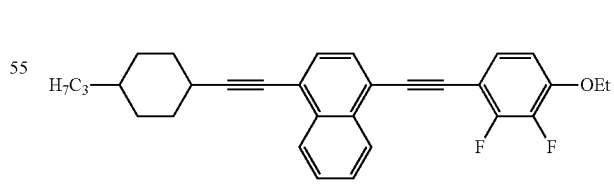

MS (EI): m/e (%)=456 (100, M$^+$), 360 (27), 331 (10).
Δ∈=−4.0
Δn=0.30
$\gamma_1$=1776 mPa·s
C 123 N 216 I 11) 1-(4-n-Butylphenylethynyl)-4-(trans-4-n-propyl-cyclohexylethynyl)naphthalene

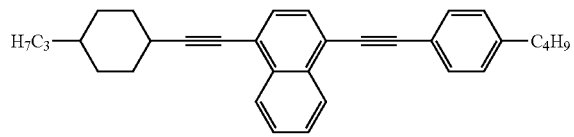

MS (EI): m/e (%)=432 (100, M$^+$), 336 (29), 291 (17), 279 (13), 265 (11).
Δ∈=+1.6
Δn=0.28
$\gamma_1$=1749 mPa·s
C 80 N 171 I 12) 1-(3,4,5-Trifluorophenylethynyl)-4-(4-n-butylphenylethynyl)naphthalene

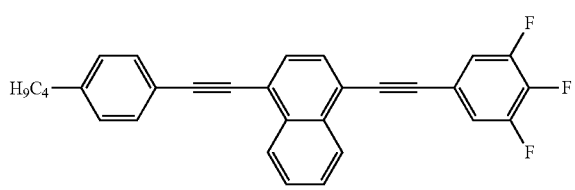

MS (EI): m/e (%)=438 (100, M$^+$), 395 (72, [M-propyl]$^+$).
Δ∈=+12.2
Δn=0.37
$\gamma_1$=964 mPa·s
C 105 N 105.1 I 13) 1-(4-Trifluoromethoxyphenylethynyl)-4-(4-n-butylphenylethynyl)naphthalene

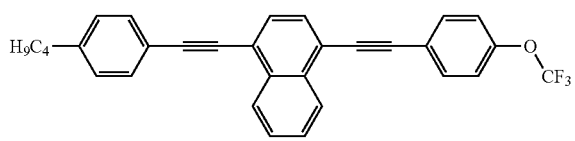

MS (EI): m/e (%)=468 (100, M$^+$), 425 (58, [M-propyl]$^+$).
Δ∈=+6.7
Δn=0.38
$\gamma_1$=1042 mPa·s
C 96 SmA (82) N 176 I 14) 1-(2-Ethyl-4-n-butylphenylethynyl)-4-(4-n-butylphenylethynyl)naphthalene

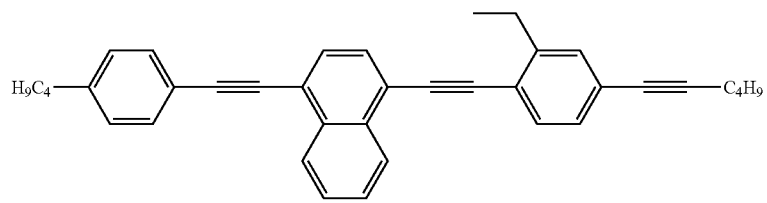

MS (EI): m/e (%)=468 (100, M$^+$), 425 (17, [M-propyl]$^+$).
Δ∈=+1.1
Δn=0.39
$\gamma_1$=1634 mPa·s
Tg −41 C 76 N 105 I 15) 1-(2-Ethyl-4-[1-hexynyl]phenylethynyl)-4-(4-n-butylphenylethynyl)naphthalene

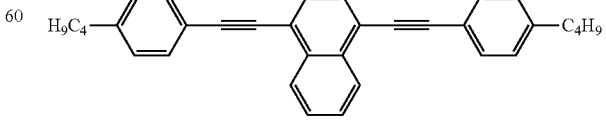

MS (EI): m/e (%)=492 (100, M$^+$), 449 (8, [M-propyl]$^+$).
Δ∈=+0.8
Δn=0.47
$\gamma_1$=6858 mPa·s
Tg −33 C 87 N 103 I 16) 1,4-Bis(2-ethyl-4-n-butylphenylethynyl)naphthalene MS (EI): m/e (%)=496 (100, M$^+$), 453 (10, [M-propyl]$^+$), 205 (10, [M-propyl-propyl]$^{2+}$).

Δ∈=+0.7
Δn=0.37
γ₁=2394 mPa·s
Tg −45 C 61 N (41) I 17) 1,4-Bis(4-n-butylphenylethynyl)anthracene

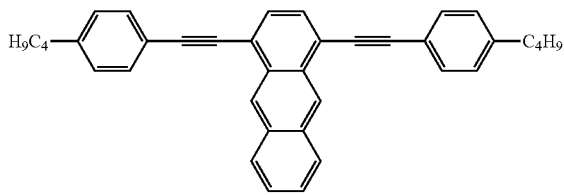

MS (EI): m/e (%)=490 (100, M⁺), 447 (21, [M-propyl]⁺), 404 (18, [M-propyl-propyl]⁺), 245 (5, M²⁺), 202 (10, [M-propyl-propyl]²⁺).
Δ∈=+1.1
Δn=0.39
γ₁=5327 mPa·s
C 132 N (111) I 18) 1-(3,4,5-Trifluorophenylethynyl)-4-(2-ethyl-4-n-butylphenylethynyl)naphthalene

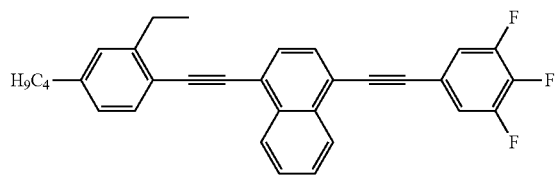

MS (EI): m/e (%)=466 (100, M⁺), 423 (72, [M-propyl]⁺), 408 (30, [M-propyl-methyl]⁺).
Δ∈=+9.6
Δn=0.36
γ₁=1630 mPa·s
C 122 I 19) 1-(4-Butylnaphthylethynyl)-4-(4-n-butylphenylethynyl)naphthalene

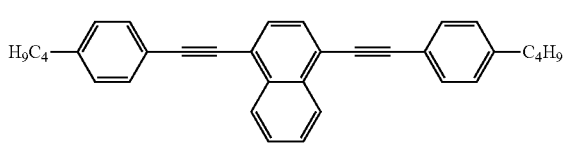

MS (EI): m/e (%)=490 (100, M⁺), 447 (66, [M-propyl]⁺), 404 (28, [M-propyl-propyl]⁺), 202 (18, [M-propyl-propyl]²⁺).

Δ∈=+0.9
Δn=0.40
γ₁=5261 mPa·s
C 114 N (110) I 20) 1,4-Bis[4-(4'-butylphenylethynyl)naphthylethynyl]benzene

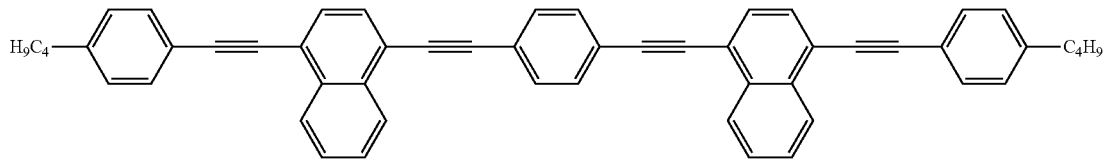

MS (EI): m/e (%)=690 (100, M⁺), 647 (13, [M-propyl]⁺), 604 (7, [M-propyl-propyl]⁺), 302 (25, [M-propyl-propyl]²⁺).
C 187 N 310 I 22) 1-(3,4,5-Trifluorophenylethynyl)-4-(2,6-difluoro-4-n-butylphenylethynyl)naphthalene

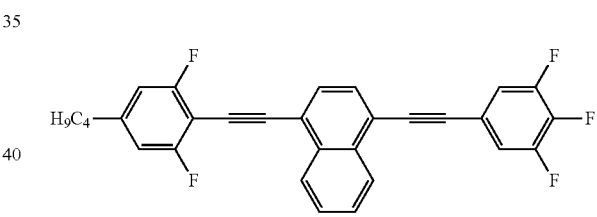

MS (EI): m/e (%)=474 (100, M⁺), 431 (55, [M-propyl]⁺).
Δ∈=+16.8
Δn=0.37
C 126 N (122) I 23) 1-(4-Trifluoromethyl-3,5-difluorophenylethynyl)-4-(2,6-difluoro-4-n-butylphenylethynyl)naphthalene

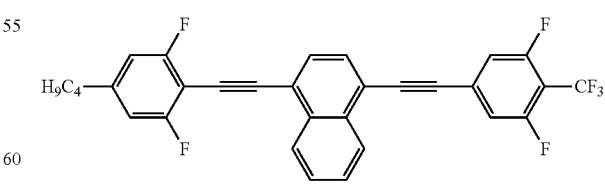

MS (EI): m/e (%)=524 (100, M⁺), 481 (69, [M-propyl]⁺).
Δ∈=+24.9
Δn=0.36
γ₁=759 mPa·s
C 136 I 24) 1-(4-Trifluoromethoxy-3,5-difluorophenylethynyl)-4-(2,6-difluoro-4-n-butylphenylethynyl)naphthalene

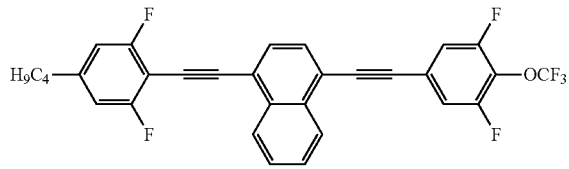

MS (EI): m/e (%)=540 (100, M$^+$), 497 (43, [M-propyl]$^+$), 428 (11, [M-propyl-trifluoromethoxy]$^+$).
C 127 N (125) I 25) 1-(4-Cyanophenylethynyl)-4-(4-n-propylphenylethynyl)naphthalene

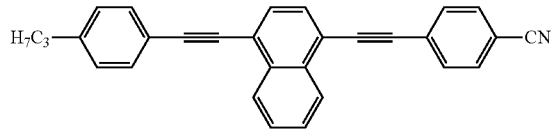

MS (EI): m/e (%)=395 (100, M$^+$), 366 (56, [M-ethyl]$^+$), 183 (12, [M-ethyl]$^{2+}$).
C 150 N 250 I 26) 1-(4-Fluoronaphthylethynyl)-4-(4-n-butylphenylethynyl)benzene

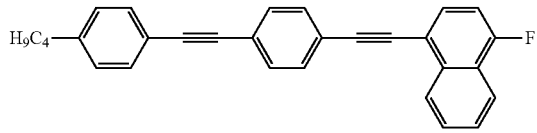

MS (EI): m/e (%)=402 (100, M$^+$), 359 (62, [M-propyl]$^+$), 179.5 (18, [M-propyl]$^{2+}$).
$\Delta\epsilon$=+5.5
$\Delta$n=0.39
$\gamma_1$=1140 mPa·s
C 123 N 133 I 27) 1-(4-n-Butylnaphthylethynyl)-4-(4-n-butylphenylethynyl)benzene

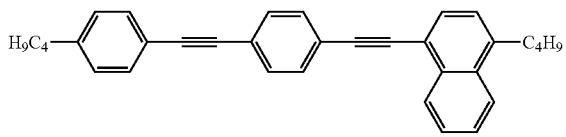

MS (EI): m/e (%)=440 (100, M$^+$), 397 (52, [M-propyl]$^+$), 354 (20, [M-propyl-propyl]$^+$), 177 (22, [M-propyl-propyl]$^{2+}$).
$\Delta\epsilon$=+2.0
$\Delta$n=0.38
$\gamma_1$=1438 mPa·s
C 105 N 137 I 28) 1-(4-n-Propylnaphthylethynyl)-4-(4-n-butylphenylethynyl)benzene

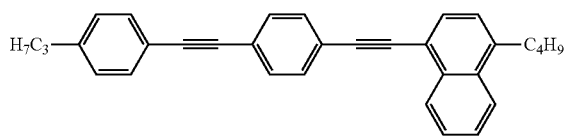

MS (EI): m/e (%)=426 (100, M$^+$), 383 (52, [M-propyl]$^+$), 354 (18, [M-propyl-ethyl]$^+$), 177 (22, [M-propyl-ethyl]$^{2+}$).
$\Delta\epsilon$=+1.9
$\Delta$n=0.39
$\gamma_1$=1820 mPa·s
C 109 N 154 I Mixture Example 1

A liquid-crystal mixture M-1 having the composition and properties as indicated in the following table is prepared. Component (1) is the compound from Synthesis Example 4).

| | Composition Compound | |
|---|---|---|
| No. | Abbreviation | |
| 1 | BCH-3F.F | 10.8% |
| 2 | BCH-5F.F | 9.00% |
| 3 | ECCP-30CF3 | 4.50% |
| 4 | ECCP-50CF3 | 4.50% |
| 5 | CBC-33F | 1.80% |
| 6 | CBC-53F | 1.80% |
| 7 | CBC-55F | 1.80% |
| 8 | PCH-6F | 7.20% |
| 9 | PCH-7F | 5.40% |
| 10 | CCP-20CF3 | 7.20% |
| 11 | CCP-30CF3 | 10.8% |
| 12 | CCP-40CF3 | 6.30% |
| 13 | CCP-50CF3 | 9.90% |
| 14 | PCH-5F | 9.00% |
| 15 | (1) | 10.0% |
| Σ | | 100.0% |
| Physical properties | | |
| T(N, I) = | | 103° C. |
| $\Delta$n (20° C., 589.3 nm) = | | 0.130 |
| $\Delta\epsilon$ (20° C., 1 kHz) = | | 5.0 |
| $\gamma_1$ (20° C.) = | | 176 mPa · s |

This liquid-crystalline mixture is used for applications in the microwave range, in particular for a phase shifter ('phased array').

For comparison, a mixture C-1 without component (1) is prepared from compound no. 1-14 of M-1, where compound no. 1-14 are present in the same relative amounts.

TABLE

| Properties of mixture M-1 and C-2 at 19 GHz (20° C.) | | | | | |
|---|---|---|---|---|---|
| Mis | $\epsilon_{r,\parallel}$ | $\epsilon_{r,\perp}$ | $\tau$ | $\tan \delta_{\epsilon,r,\parallel}$ | $\tan \delta_{\epsilon,r,\perp}$ | $\eta$ |
| M-1 | 2.60 | 2.34 | 0.101 | 0.0041 | 0.0127 | 7.95 |
| C-1 | 2.49 | 2.30 | 0.079 | 0.0048 | 0.0139 | 5.70 |

The tuneability τ and the material quality η are improved compared with comparative mixture C-1.

Further combinations of the embodiments and variants of the invention in accordance with the description also arise from the claims below.

The invention claimed is:

1. A compound of formula I $$R^1-(A^1-Z^1)_m-A^2-\!\!\!\equiv\!\!\!-A^3-\!\!\!\equiv\!\!\!-A^4-(Z^5-A^5)_n-R^2 \qquad I$$

in which
A$^{1-5}$, independently of one another, denote
a) a radical of the formula

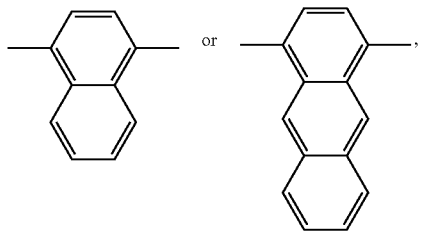

b) 1,4-phenylene, in which one or more CH groups are optionally replaced by N,
c) trans-1,4-cyclohexylene or cyclohexenylene, in which one or two non-adjacent CH$_2$ groups are optionally replaced by —O— and/or —S— and in which H are optionally replaced by F,
or
d) 1,4-bicyclo[2.2.2]octylene, cyclobut-1,3-diyl, spiro [3.3]heptane-2,6-diyl, thiophene-2,5-diyl, thiophene-2,4-diyl, furan-2,5-diyl, furan-2,4-diyl,

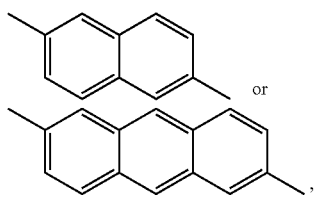

and in which groups a), b), c) and d),
one or more H atoms are also optionally replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group,
and where
the compound of formula I comprises at least one radical according to a),
R$^1$ denotes a halogenated or unsubstituted alkyl radical having 1 to 15 C atoms, in which one or more CH$_2$ groups are each optionally replaced, independently of one another, by —C≡C—, —CH═CH—, —CF═CF—, —CF═CH—, —CH═CF—, —(CO)O—, —O(CO)—, —(CO)— or —S— in such a way that O or S atoms are not linked directly to one another,
R$^2$ denotes an alkyl radical having 2 to 5 C atoms, in which one or more CH$_2$ groups are each optionally replaced, independently of one another, by —C≡C—, —CH═CH—, —CF═CF—, —CF═CH—, —CH═CF—, —(CO)O—, —O(CO)— or —(CO)— in such a way that O atoms are not linked directly to one another, or F, CF$_3$, OCF$_3$, SCN, NCS or SF$_5$,
Z$^1$, Z$^5$, independently of one another, denote a single bond, —C≡C—, —CH═CH—, —CH$_2$O—, —(CO)O—, —CF$_2$O—, —CF$_2$CF$_2$—, —CH$_2$CF$_2$—, —CH$_2$CH$_2$—, —(CH$_2$)$_4$—, —CH═CF— or —CF═CF—, where asymmetrical bridges may be oriented to either direction, and
m, n, independently of one another, denote 0, 1 or 2,
where
the compound of formula I-X-2

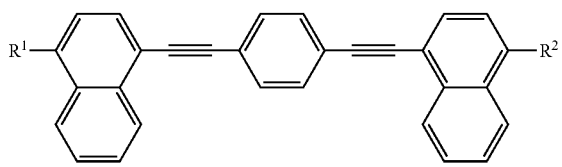

in which
R$^1$ and R$^2$ simultaneously denote n-C$_4$H$_9$,
are excluded.

2. A compound according to claim 1, wherein at least one of A$^2$, A$^3$ and A$^4$ denotes an optionally substituted 1,4-naphthylene radical or 1,4-anthracenylene radical.

3. A compound according to claim 1, which contains one or two optionally substituted 1,4-naphthylene radicals or 1,4-anthracenylene radicals.

4. A compound according to claim 1, wherein m and n are 0.

5. A liquid-crystal medium, comprising one or more compounds of formula I

in which
A$^{1-5}$, independently of one another, denote
a) a radical of the formula

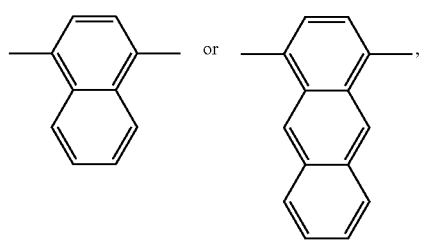

b) 1,4-phenylene, in which one or more CH groups are optionally replaced by N,
c) trans-1,4-cyclohexylene or cyclohexenylene, in which one or two non-adjacent CH$_2$ groups are optionally replaced by —O— and/or —S— and in which H are optionally replaced by F, or
d) 1,4-bicyclo(2,2,2)octylene, cyclobut-1,3-diyl, spiro [3.3]heptane-2,6-diyl, thiophene-2,5-diyl, thiophene-2,4-diyl, furan-2,5-diyl, furan-2,4-diyl,

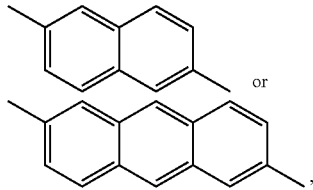

or and in which groups a), b), c) and d),
one or more H atoms are also optionally replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group, and where
the compound of formula I comprises at least one at least one radical according to a),
R$^1$ and R$^2$ each, independently of one another, denote a halogenated or unsubstituted alkyl radical having 1 to 15 C atoms, in which one or more CH$_2$ groups are each optionally replaced, independently of one another, by —C≡C—, —CH=CH—, —CF=CF—, —CF=CH—, —CH=CF—, —(CO)O—, —O(CO)—, —(CO)— or —O— in such a way that O atoms are not linked directly to one another,
or F, Cl, Br, CN, CF$_3$, OCF$_3$, SCN, NCS or SF$_5$,
Z$^1$, Z$^5$, independently of one another, denote a single bond, —C≡C—, —CH=CH—, —CH$_2$O—, —(CO)O—, —CF$_2$O—, —CF$_2$CF$_2$—, —CH$_2$CF$_2$—, —CH$_2$CH$_2$—, —(CH$_2$)$_4$—, —CH=CF— or —CF=CF—, where asymmetrical bridges may be oriented to either direction, and
m, n, independently of one another, denote 0, 1 or 2.

6. A liquid-crystal medium according to claim 5, additionally comprising one or more compounds of formula II:

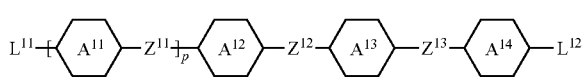

in which
L$^{11}$ denotes R$^{11}$ or X$^{11}$,
L$^{12}$ denotes R$^{12}$ or X$^{12}$,
R$^{11}$ and R$^{12}$, independently of one another, denote unfluorinated alkyl or unfluorinated alkoxy having 1 to 17 C atoms or unfluorinated alkenyl, unfluorinated alkenyloxy, unfluorinated alkynyl, or unfluorinated alkoxyalkyl having 2 to 15 C atoms,
X$^{11}$ and X$^{12}$, independently of one another, denote F, Cl, Br, —CN, —NCS, —SCN, —SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms, and p denotes 0 or 1,
Z$^{11}$ to Z$^{13}$, independently of one another, denote trans-CH=CH—, trans-CF=CF—, —C≡C— or a single bond, and

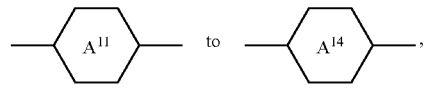

independently of one another, denote
a) 1,4-phenylene, in which one or more CH groups are optionally replaced by N,
b) trans-1,4-cyclohexylene or cyclohexenylene, in which one or two non-adjacent CH$_2$ groups are optionally replaced by —O— and/or —S— and in which H are optionally replaced by F,
and in which groups a) and b),
one or more H atoms are also optionally replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group, or a C$_3$-C$_6$ cycloalkyl.

7. A liquid-crystal medium according to claim 5, in which the concentration of the compounds of formula I is in total 5% to 95%.

8. A liquid-crystal medium, comprising one or more compounds of formula I

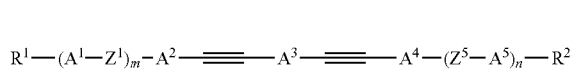

in which
A$^{1-5}$, independently of one another, denote
a) a radical of the formula

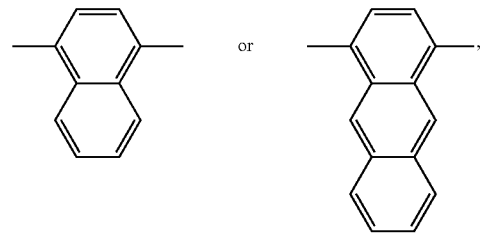

or b) 1,4-phenylene, in which one or more CH groups are optionally replaced by N,
c) trans-1,4-cyclohexylene or cyclohexenylene, in which one or two non-adjacent CH$_2$ groups are optionally replaced by —O— and/or —S— and in which H are optionally replaced by F, or
d) 1,4-bicyclo[2.2.2]octylene, cyclobut-1,3-diyl, Spiro [3.3]heptane-2,6-diyl, thiophene-2,5-diyl, thiophene-2,4-diyl, furan-2,5-diyl, furan-2,4-diyl,

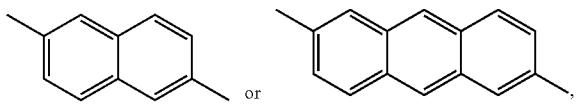

and in which groups a), b), c) and d), one or more H atoms are also optionally replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group, and where the compound of formula I comprises at least one radical according to a), R$^1$ and R$^2$ each, independently of one another, denote a halogenated or unsubstituted alkyl radical having 1 to 15 C atoms, in which one or more CH$_2$ groups are each optionally replaced, independently of one another, by —C≡C—, —CH═CH—, —CF═CF—, —CF═CH—, —CH═CF—, —(CO)O—, —O(CO)—, —(CO)—, —O— or —S— in such a way that O or S atoms are not linked directly to one another, or F, Cl, Br, CN, CF$_3$, OCF$_3$, SCN, NCS or SF$_5$, Z$^1$, Z$^5$, independently of one another, denote a single bond, —C≡C—, —CH═CH—, —CH$_2$O—, —(CO)O—, —CF$_2$O—, —CF$_2$CF$_2$—, —CH$_2$CF$_2$—, —CH$_2$CH$_2$—, —(CH$_2$)$_4$—, —CH═CF— or —CF═CF—, where asymmetrical bridges may be oriented to either direction, and m, n, independently of one another, denote 0, 1 or 2, where compounds of formula I-X-1

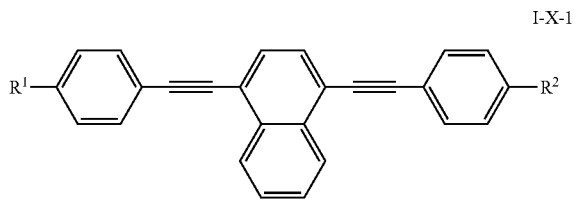

I-X-1 in which

R$^1$ and R$^2$ are each simultaneously CH$_3$, n-C$_6$H$_{11}$, CF$_3$, F or OCH$_3$, or R$^1$ denotes tert-butyl and R$^2$ denotes —CN, and the compound of formula I-X-2

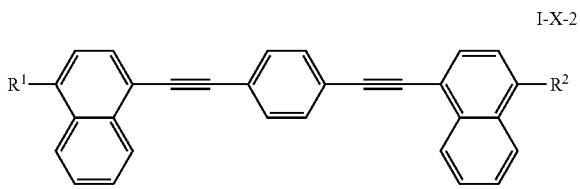

I-X-2 in which

R$^1$ and R$^2$ simultaneously denote n-C$_4$H$_9$, are excluded.

9. A process for preparing a liquid-crystal medium according to claim 6, comprising mixing one or more compounds of formula I with one or more compounds of formula II, and optionally with one or more further compounds and optionally with one or more additives.

10. A component for high-frequency technology, comprising a liquid-crystal medium according to claim 5.

11. A component according to claim 10, which is one or more functionally connected phase shifters.

12. A component for high-frequency technology, comprising a liquid-crystal medium according to claim 8.

13. A phase-controlled group antenna, comprising one or more components according to claim 10.

14. A liquid-crystal medium, comprising one or more compounds according to claim 1.

15. A liquid-crystal medium according to claim 5, wherein in at least one of the one or more compounds of formula I, at least one of A$^2$, A$^3$ and A$^4$ denotes an optionally substituted 1,4-naphthylene radical or 1,4-anthracenylene radical.

16. A liquid-crystal medium according to claim 5, wherein at least one of the one or more compounds of formula I contains one or two optionally substituted 1,4-naphthylene radicals or 1,4-anthracenylene radicals.

17. A liquid-crystal medium according to claim 5, wherein in at least one of the one or more compounds of formula I, m and n are 0.

18. A liquid-crystal medium according to claim 8, wherein in at least one of the one or more compounds of formula I, at least one of A$^2$, A$^3$ and A$^4$ denotes an optionally substituted 1,4-naphthylene radical or 1,4-anthracenylene radical.

19. A liquid-crystal medium according to claim 8, wherein at least one of the one or more compounds of formula I contains one or two optionally substituted 1,4-naphthylene radicals or 1,4-anthracenylene radicals.

20. A liquid-crystal medium according to claim 8, wherein in at least one of the one or more compounds of formula I, m and n are 0.

* * * * *